(12) United States Patent  
Trickett

(10) Patent No.: US 7,479,130 B2
(45) Date of Patent: Jan. 20, 2009

(54) APPARATUS AND METHOD FOR AUTOLOGOUS NORMOVOLEMIC HEMODILUTION

(75) Inventor: James R. Trickett, Euclid, OH (US)

(73) Assignee: University Hospitals of Cleveland Case Western Reserve University, Cleveland, OH (US)

( * ) Notice: Subject to any disclaimer, the term of this patent is extended or adjusted under 35 U.S.C. 154(b) by 126 days.

(21) Appl. No.: 11/318,286

(22) Filed: Dec. 23, 2005

(65) Prior Publication Data

US 2006/0142707 A1 Jun. 29, 2006

Related U.S. Application Data

(60) Provisional application No. 60/639,246, filed on Dec. 27, 2004.

(51) Int. Cl.
*A61B 19/00* (2006.01)
*A61M 37/00* (2006.01)

(52) U.S. Cl. .................. 604/403; 604/416; 604/6.15

(58) Field of Classification Search ....... 604/4.01–6.16, 604/403–416, 319–321, 132–143, 317, 573; 128/214; 422/44–48
See application file for complete search history.

(56) References Cited

U.S. PATENT DOCUMENTS

| | | | |
|---|---|---|---|
| 3,809,087 A * | 5/1974 | Lewis, Jr. ................. | 604/134 |
| 4,006,745 A | 2/1977 | Sorenson et al. | |
| 4,033,345 A | 7/1977 | Sorenson et al. | |
| 4,047,526 A * | 9/1977 | Reynolds et al. ........... | 604/6.15 |
| 4,501,581 A | 2/1985 | Kurtz et al. | |
| 4,772,256 A | 9/1988 | Lane et al. | |
| 4,775,360 A | 10/1988 | Lane et al. | |
| 4,898,572 A | 2/1990 | Surugue nee Lasnier et al. | |
| 4,930,644 A * | 6/1990 | Robbins, III ................ | 215/382 |
| 5,149,325 A | 9/1992 | Telang et al. | |
| 5,201,703 A | 4/1993 | Gentelia et al. | |
| 5,372,593 A | 12/1994 | Boehringer et al. | |
| 5,380,314 A * | 1/1995 | Herweck et al. ............ | 604/403 |
| 5,658,271 A * | 8/1997 | Loubser ..................... | 604/410 |
| 5,941,635 A * | 8/1999 | Stewart .................... | 366/165.5 |
| 6,582,386 B2 | 6/2003 | Min et al. | |
| 6,626,857 B1 | 9/2003 | Ohta et al. | |

* cited by examiner

*Primary Examiner*—Leslie R Deak
*Assistant Examiner*—Phil Wiest
(74) *Attorney, Agent, or Firm*—Renner, Otto, Boisselle & Sklar, LLP

(57) ABSTRACT

A system and method for autologous normovolemic hemodilution (ANH) are disclosed. The system can include a vacuum canister, which is sized to accept donor bags of a predetermined capacity. The vacuum canister is connected to a vacuum source which applies a suction to the donor bag within the canister. The system can include a canister having a self-generated vacuum, which includes compressible sidewalls that are spring-loaded to provide negative pressure needed to collect blood from a patient without the use of a gravity-induced siphon gradient. Also disclosed are ANH systems and kits that rely on a gravity-induced siphon gradient for blood collection.

8 Claims, 5 Drawing Sheets

APPARATUS AND METHOD FOR AUTOLOGOUS NORMOVOLEMIC HEMODILUTION

CROSS-REFERENCE TO RELATED APPLICATIONS

This application claims priority under 35 U.S.C. §119 of U.S. Provisional Application No. 60/639,246, filed Dec. 27, 2004, the entire disclosure of which is incorporated herein by reference.

TECHNICAL FIELD

The present invention relates generally to the field of blood collection and transfusion and, more particularly, to an apparatus and method for autologous normovolemic hemodilution.

BACKGROUND

Autologous blood transfusions, which are defined as the reinfusion of the patient's own blood, continue to be used in surgical settings. One type of autologous blood transfusion involves preoperative donation and storage of a patient's blood. In such a process, a patient's blood is collected, typically over a period of weeks or months, and stored for transfusion at the time of surgery. While preoperative autologous blood donation/transfusion is popular, the process suffers from some drawbacks. These drawbacks can include limitations in the amount of blood that can be collected over a period of time, wasting of pre-donated blood because it is not needed or expired, and transfusion of the wrong blood due to clerical errors.

In response to these shortcomings, intraoperative hemodilution (also referred to as autologous normovolemic hemodilution or ANH) has grown in popularity. ANH includes the removal or collection of blood (typically just before or at the start of a surgical procedure) with the simultaneous infusion of appropriate cell-free solution(s) to maintain intravascular volume prior to surgical blood loss. The previously collected patient's blood is reinfused during or after surgery, as needed, to maintain a desired post-ANH hemoglobin concentration. Typically, the anesthesiologist is responsible for the ANH procedure. ANH allows for collection and reinfusion of a greater volume of blood than preoperative autologous procedures because the patient is typically sedated and often is on a ventilator. ANH reduces red blood cell loss because the blood lost during surgery has a lower hematocrit (the percentage of whole blood that is comprised of red blood cells).

Conventional devices used for ANH typically include a standard blood donation/transfer bag, e.g., a 500 cc bag, and rely on gravity for blood drainage and collection. Such conventional transfer bag devices require long tubing to create the necessary siphon gradient for blood drainage. In order to accommodate the long tubing, the bags are often placed far away from the patient making it more difficult to monitor the progress of the blood drainage. This can be problematic for several reasons. The use of long tubing increases the likelihood of clotting within the tubing. Having the bag out of sight increases the chances of collecting too much blood in a single bag, which could cause clotting, forgetting to agitate the bag periodically to mix the collected blood with an anticoagulant within the bag, and potentially knocking over the bag or pulling the line out of the bag and/or patient.

SUMMARY OF THE INVENTION

According to one aspect of the invention, there is provided an autologous normovolemic hemodilution (ANH) blood collection device including a canister that defines an internal volume for receiving a blood collection bag, the canister including a blood inlet port and a vacuum inlet port. The canister is openable and provides a substantially air-tight seal around the blood collection bag.

According to another aspect of the present invention, there is provided an autologous normovolemic hemodilution (ANH) blood collection device including a canister having resilient, compressible sidewalls and a compression device operative to compress the canister. The resilient canister sidewalls are operative to return to an decompressed state following compression, thereby generating a negative pressure within the canister of sufficient magnitude to draw blood from a patient.

According to another aspect of the invention, there is provided a device for collecting blood from a patient through a blood collection line, the device including a canister in fluid communication with the patient, the canister being configured to self-generate an internal negative pressure of sufficient magnitude to draw blood from the patient.

Although various features are described and are illustrated in respective drawings/embodiments, it will be appreciated that features of a given drawing or embodiment may be used in one or more other drawings or embodiments of the invention.

The foregoing and other features of the invention are hereinafter more fully described and particularly pointed out in the claims, the following description setting forth in detail certain illustrative embodiments of the invention, these being indicative, however, of but a few of the various ways in which the principles of the invention may be employed.

BRIEF DESCRIPTION OF DRAWINGS

These and further features of the present invention will be apparent with reference to the following description and drawings, wherein.

DISCLOSURE OF INVENTION

Figure 1A:
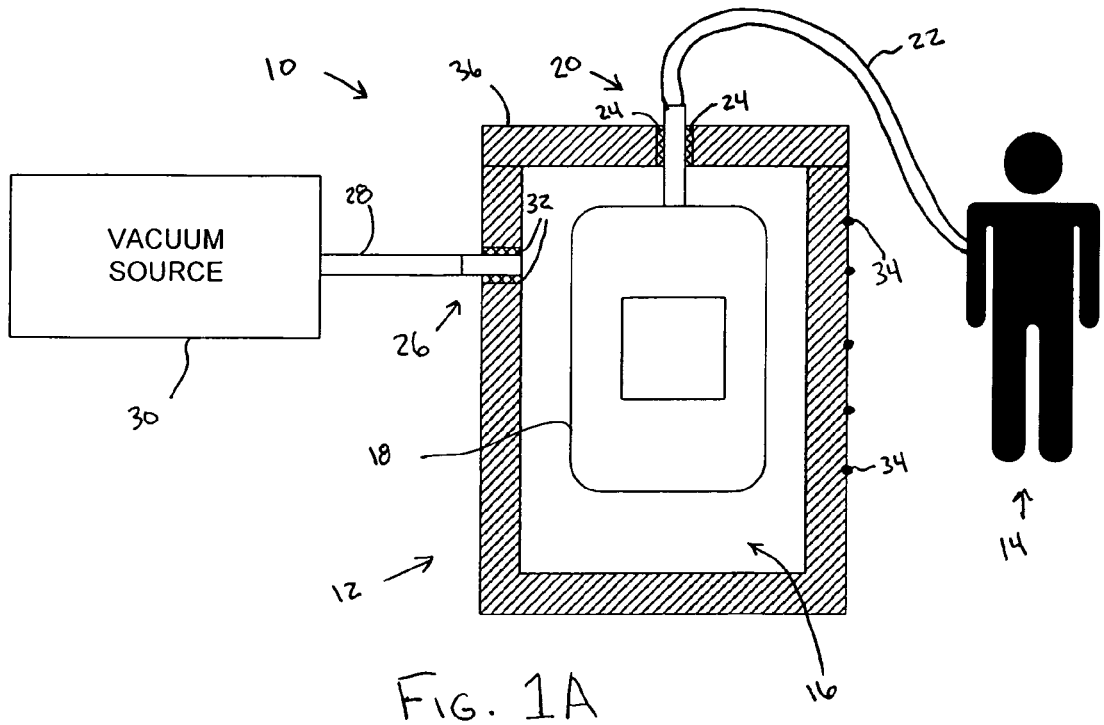
FIG. 1A and FIG. 1B are diagrammatic side view illustrations of an autologous normovolemic hemodilution (ANH) blood collection device and system in accordance with an exemplary embodiment of the present invention.

In the detailed description that follows, corresponding components have been given the same reference numerals regardless of whether they are shown in different embodiments of the present invention. To illustrate the present invention in a clear and concise manner, the drawings may not necessarily be to scale and certain features may be shown in somewhat schematic form.

An exemplary autologous normovolemic hemodilution (ANH) blood collection system according to the present invention is indicated generally by the numeral 10 in the accompanying drawings. Artisans will appreciate that ANH generally includes the removal or collection of a patient's blood (typically just before or at the start of a surgical procedure) with the simultaneous infusion of appropriate cell-free solution(s) to maintain intravascular volume prior to or concurrent with surgical blood loss. The previously collected patient's blood is re-infused during or after surgery, as needed, to maintain the desired post-ANH hemoglobin concentration. While the present invention is being described in connection with ANH blood collection, it is to be appreciated that the present invention is applicable. Further, while the present invention is being described with reference to blood collection, it is to be appreciated that the present invention may find application in conjunction with other fluid collection without departing from the scope of the present invention.

As described below with respect to exemplary embodiments, the ANH blood collection system 10 includes a blood collection device 12 (also referred herein as a canister) that can collect or otherwise draw blood from a patient 14 without the use of a gravity-induced siphon gradient. As is discussed more fully below, the blood collection device for canister can be disposed at a vertical height that is at or above the vertical height of a "draw point" on a patient (e.g., the point on the patient from which blood is drawn, such as the arm or leg).

Figure 1B:
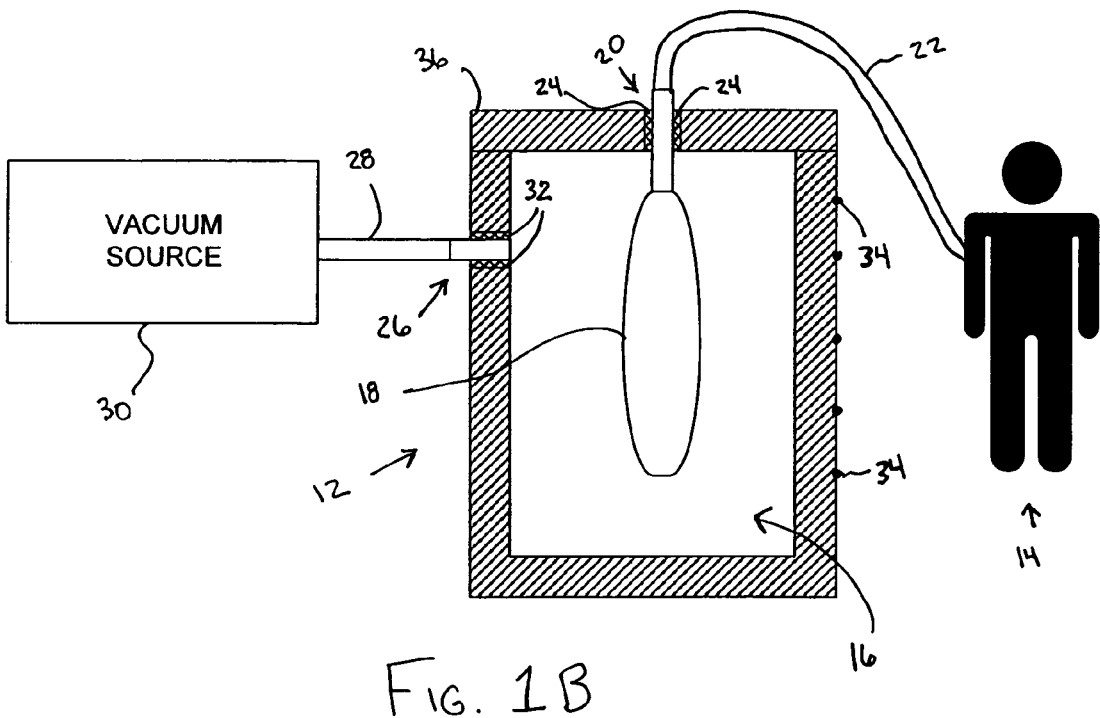

With reference to FIG. 1A and FIG. 1B, an ANH blood collection system 10 is provided. The system 10 includes a blood collection device 12 (also referred to herein as a canister or a vacuum canister). The canister 12 includes substantially rigid walls (e.g., sidewalls, a bottom wall, and a top wall or cover), which define an internal volume 16 within which a donor or collection bag 18 is received. The donor bag 18 can be a conventional donor bag, such as a standard 513 cc (cubic centimeters) bag. Typically, the donor bag 18 includes a predetermined amount of anticoagulant (e.g., 63 cc) disposed therein to prevent or minimize clotting of blood as it is collected within the bag. The canister 12 includes or otherwise defines a blood inlet port 20 through which blood is drawn from the patient 14 through flexible tubing 22 (also referred to as a draw line) into the collection bag 18 through the blood inlet port 20. The blood inlet port 20 includes suitable sealing means 24, such as a rubber seal, a foam rubber seal, a gasket or the like. The sealing means 24 facilitate a substantially air-tight seal that is suitable for supporting a vacuum of at least about −25 millimeters of mercury (mm of Hg), for example.

The canister 12 further includes or otherwise defines a vacuum inlet port 26, which sealably receives flexible tubing 28 that is connected to a vacuum source 30. As is discussed above with respect to the blood input port, the vacuum inlet port includes suitable sealing means 32. The vacuum source 30 can include any suitable vacuum source, such as those commonly found in many hospital and operating rooms. The vacuum source 30 evacuates the internal volume 16 of the canister 12 and pulls the collection bag 18, disposed therein, apart, thereby creating a negative pressure for drawing blood from the patient 14. Optionally, the system can include a regulator, which can be integral to the vacuum source 30 or disposed between the vacuum source 30 and the canister 12 in communication with the vacuum line. The regulator serves to control the vacuum generated by the vacuum source, often including a break point setting for safety (e.g., to avoid an unduly high negative pressure that could collapse a patient's blood vessel).

The canister 12 can be made from a substantially transparent or substantially translucent material, such as sturdy plastic or other polymer that allows for viewing of the contents of the donor bag through the canister. Alternatively, the canister can be made of a relatively opaque material. The canister can include graduated markings 34 (e.g., volume indicating markings) on the outer portion. The markings aid a user in determining the volume of blood and anticoagulant within the collection bag. As is discussed below, the canister can define an internal volume having a variety of shapes or geometries.

Figure 2A:
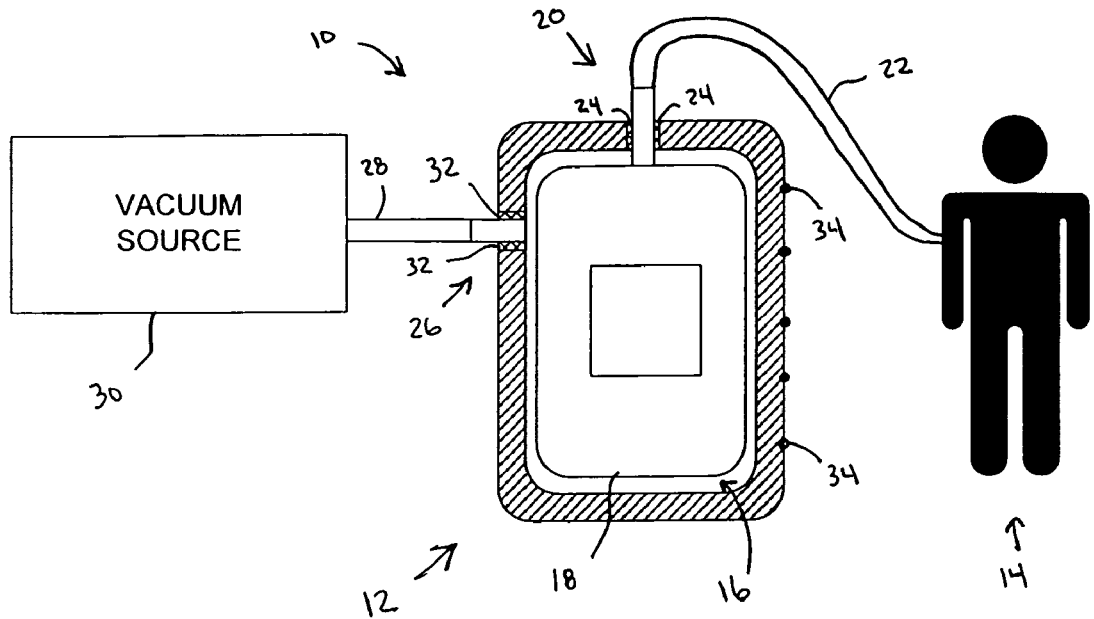
FIG. 2A and FIG. 2B are diagrammatic side view illustrations of an ANH blood collection device and system in accordance with another exemplary embodiment of the invention.
Figure 2B:
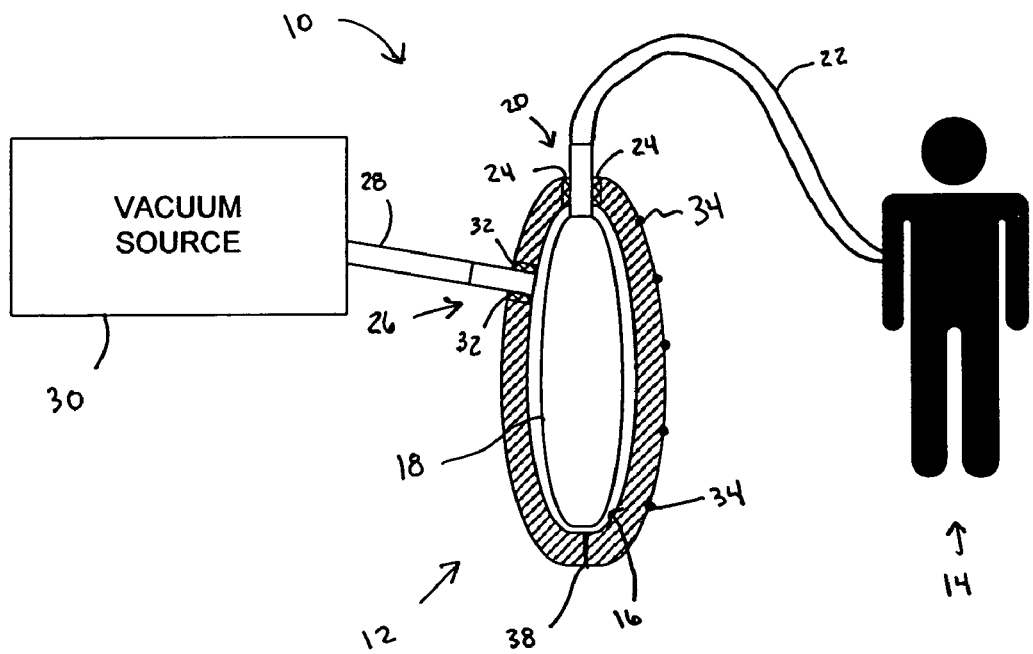

The canister is openable and closeable, and can be closed using any suitable closure mechanism, such as cooperative threaded portions, a snap-fit mechanism and the like. The canister, in a closed configuration, is sealed to support a suitable vacuum therein (e.g., a vacuum sufficient to create a negative pressure of at least about −25 mm of Hg within the collection bag), while being openable for insertion and removal of collection bags. In one embodiment (illustrated in FIGS. 1A and 1B), the canister includes a top portion 36 that is removable for insertion and removal of donor bags. Alternatively, the canister includes a clamshell design (illustrated, for example, in FIGS. 2A and 2B) that opens along a hinge 38 into a pair of halves or portions. Such a clamshell design can include a seal substantially around the perimeter of the canister so that the canister can support a vacuum sufficient to pull the collection bag apart.

In one embodiment, the canister is formed such that the internal volume closely corresponds to the volume of a collection bag that is filled to a desired volume (e.g., approximately 513 cc). Such a design provides an additional check to limit the filling of or otherwise to prevent overfilling of a collection bag (and therefore to avoid or minimize clotting within the bag. The clamshell canister can include appropriate hinges 38 on or along one of its edges (e.g., its bottom edge). Optionally, the canister may be designed to provide or otherwise define an adjustable internal volume for closely receiving collection bags of varying volume.

In this exemplary embodiment, the ANH system eliminates the need for use of gravity to collect blood by way of a siphon gradient. Therefore, the canister can be disposed at a vertical height that is approximately even with or above the vertical height of the draw point on the patient. In addition, the drawline 22 can be of a shorter length, thereby further reducing the potential for clotting during blood collection.

Figure 3:
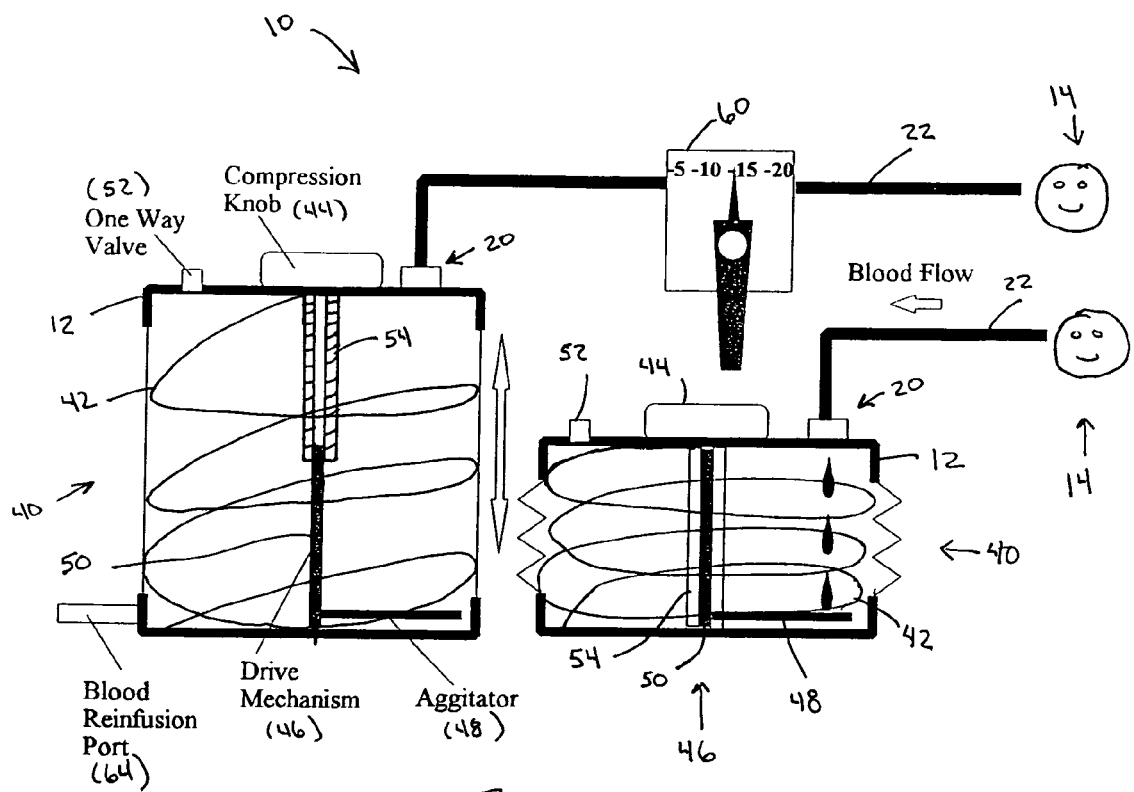
FIG. 3 is a diagrammatic illustration of an ANH blood collection device shown in a compressed condition and a decompressed condition in accordance with another exemplary embodiment of the present invention.

With reference now to FIG. 3, an ANH blood collection system 10 includes a blood collection device 12 that provides a self-generated vacuum (e.g., a negative pressure that is sufficient to draw blood from a patient 14 through a length of tubing 22 when the blood collection device 12 is at a height that is (i) somewhat lower than the draw point on the patient, (ii) at approximately the same vertical height as the draw point on the patient, or (iii) somewhat vertically higher than the draw point on the patient).

The blood collection device 12 includes sidewalls 40 that are compressible or otherwise collapsible. For purposes of this discussion, FIG. 3 illustrates the device in a compressed state on the right of the figure and in a decompressed state on the left of the figure. The sidewalls 40 can be made of a flexible plastic or plastic-like material, and include a resilient spring-like coil member 42 integrally formed with the sidewalls 40. The coil member can be made of plastic, a metal or another suitable material. The blood collection device 12 includes a compression device 44 (such as a compression knob or other device for mechanically compressing the device), which can be attached to an internal drive mechanism 46. If the collection device 12 is in an decompressed state (shown on the left of FIG. 3), the compression knob can be turned or otherwise actuated to compress the sidewalls of the collection device (as shown on the right of FIG. 3).

In one embodiment, the device 12 includes an agitator 48 that is connected to a lower portion 50 of the drive mechanism 46. The device 12 optionally includes a de-airing port 52, for example, a one-way valve, which releases air from the internal volume of the device 12 as the device is compressed. The drive mechanism for 46 includes a lower portion 50 for and a cooperative upper portion 54. In one embodiment, the lower and upper portions 50, 54 are cooperative threaded portions, for example a female threaded portion 54 and a male threaded portion 50. Once the device 12 is in the compressed state, the internal volume of the collection device 12 has been substantially evacuated. Once the device is compressed and the draw line 22 is coupled to the blood inlet port 20 and the patient 14, the coil member 42 of the sidewalls provides a force to decompress or otherwise expand the device 12, thereby generating a negative pressure within the device to draw blood from the patient into the internal volume of the collection device. As the device decompresses, the lower portion 50 of the drive mechanism 46 rotates with respect to the upper portion 54, thereby activating the agitator, which is attached to the lower portion 50. This agitation aids in preventing clotting of blood collected within the collection device. The collection device can be formed to collect a predetermined volume of anticoagulant, which is predisposed within the device before collection, and collected blood (e.g., approximately 513 cc of blood and anticoagulant). In one embodiment, the internal portions (e.g., the sidewalls, the drive mechanism and the agitator) of the collection device incorporate the use a biocompatible coating, for example, covalently bonded heparin or the like, to inhibit clotting or other complement activations.

The system 10 can include a pressure regulator 60, which is disposed along the draw line 20 between the patient 14 and the collection device 12. The regulator serves to adjust the vacuum pressure generated by the collection device, for example, to prevent collapsing of a patient's blood vessel due to an excessive negative pressure.

In this embodiment, an external vacuum source is not required, which eliminates the need for vacuum tubing. In addition, as is mentioned above, the collection device 12 can be disposed at approximately the same or higher vertical height as compared to the drawpoint on the patient. As shown in FIG. 3, the collection device can include a blood reinfusion port 64 disposed adjacent the bottom portion of the device. The blood reinfusion port allows for relatively easy reinfusion of collected blood into the patient at the appropriate time. Optionally, the compression knob 44 can be used to apply additional positive pressure within the collection device to aid in blood reinfusion.

Figure 5:
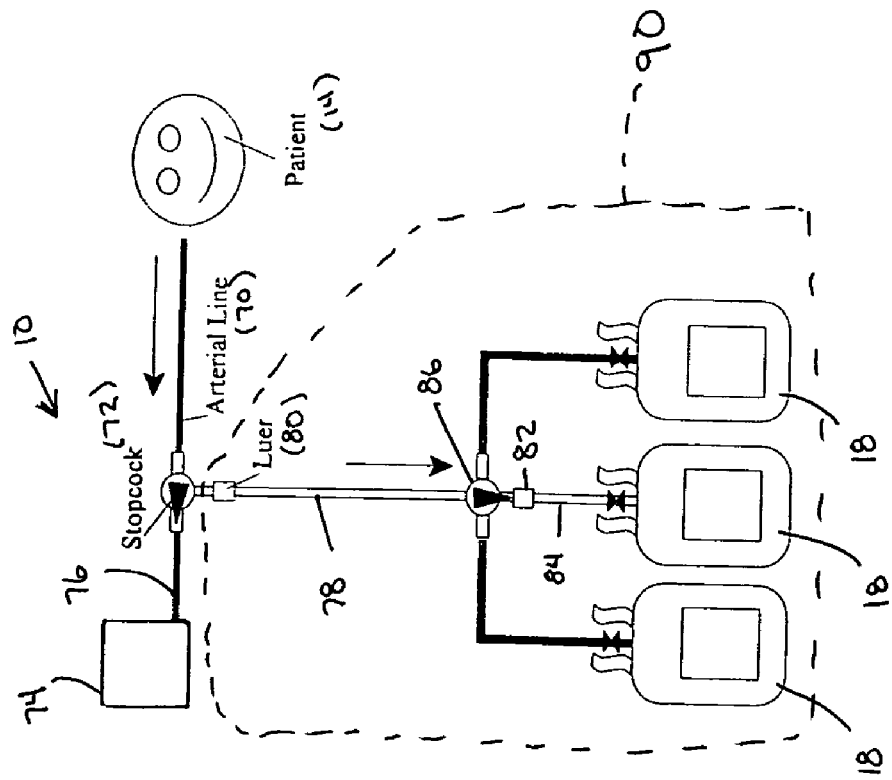
FIG. 5 is a diagrammatic illustration of an ANH blood collection device, kit and system in accordance with another embodiment of the present invention.
Figure 4:
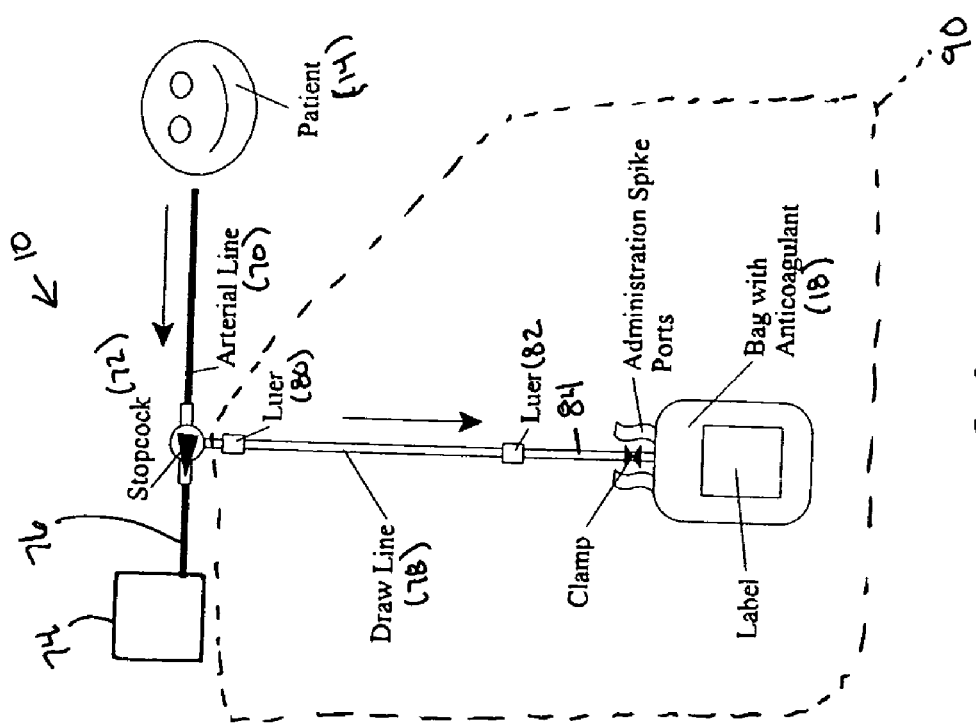
FIG. 4 is a diagrammatic illustration of an ANH blood collection device, kit and system in accordance with another exemplary embodiment of the present invention.

FIG. 4 and FIG. 5 illustrate exemplary embodiments of an ANH blood collection system 10 in accordance with aspects of the present invention. FIG. 4 illustrates a system in which a single collection bag 18 can be filled at one time, while FIG. 5 illustrates a system in which one or more collections bags 18 can be filled at one time. In each of the illustrated embodiments, the system includes tubing 70 (e.g., an arterial line) that extends from the draw point on the patient to a first stopcock 72 or other fluid directing device. The stopcock includes a number of ports for directing fluid in different directions. Optionally, one port is connected to a transducer 74 or other pressure monitoring device via tubing 76. The stopcock 72 can be positioned to direct blood to the pressure sensor 74 for periodic monitoring of a patient's blood pressure. The system can include a mechanism for continuous blood pressure monitoring (e.g., a dual lumen arterial line).

One port is connected to a draw line 78 via a luer connection 80. The draw line 78 can be connected to a collection bag 18 via an additional luer connection 82. In the embodiment illustrated in FIG. 4, the draw line 78 includes a luer connection at both the distal 82 and proximal 80 ends. The collection bag, which typically includes anticoagulant therein, includes a transfer line 84 with a luer connection 82 to connect to or otherwise mate with the luer connection on the proximal end of the draw line. Each luer connection can include, for example, a standard luer fitting, a luer-lock fitting or any threaded, substantially water-tight connector. The use of luer connections facilitates fast removal and installation of collection bags, while providing a mechanically secure and substantially water-tight connection between the collection bag and the draw line. It is to be appreciated that the portion of the system that is designated generally as 90 can be thought of as an ANH kit.

FIG. 5 illustrates an alternative embodiment in which one or more collection bags 18 can be filled. This embodiment is similar to the embodiment described above and illustrated in FIG. 4. The draw line 78 includes a luer connection 80 at its distal end, but it also includes a stopcock 86 or other fluid directing device along with a luer connection 82 at its proximal end. This additional stopcock facilitates simultaneous filling of one or more collection bags. It is to be appreciated that the portion of the system that is designated generally as 90 can be thought of as an ANH kit.

Figures 6A, 6B, 6C:
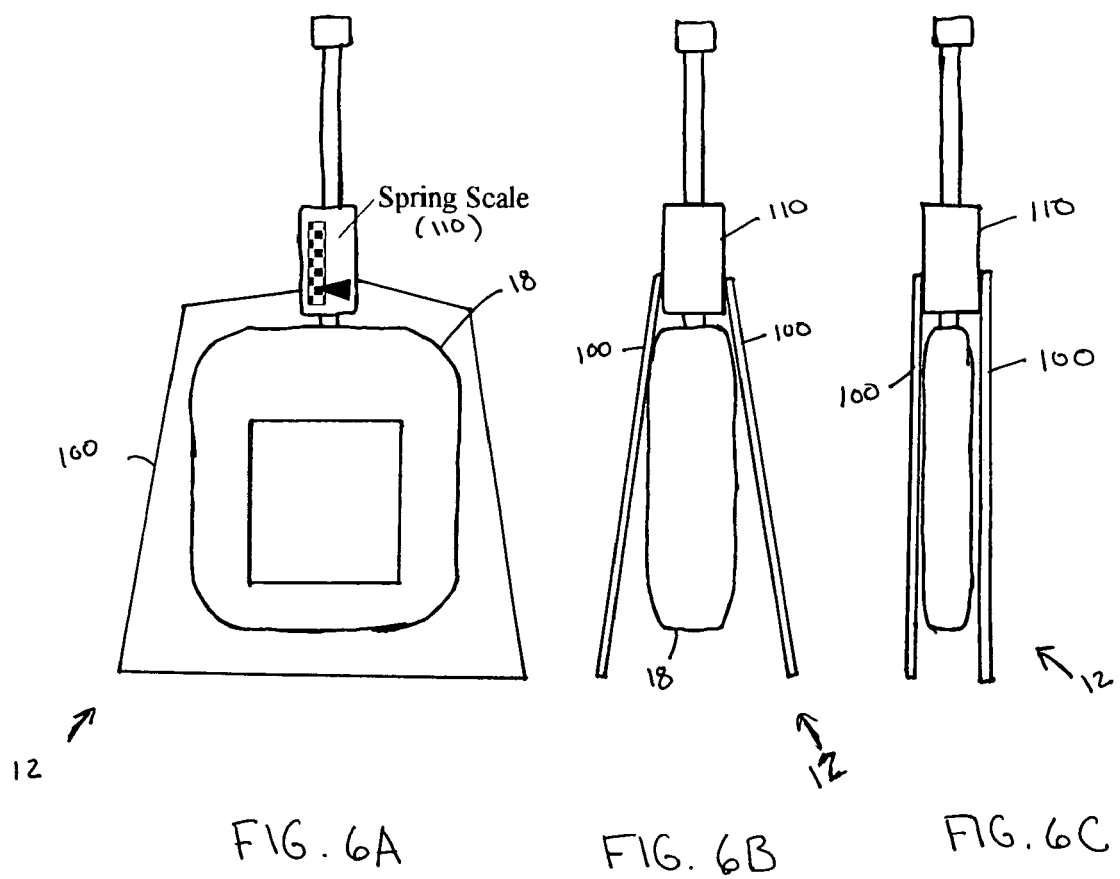
FIGS. 6A-6C are diagrammatic side view illustrations of an ANH blood collection device usable in connection with the systems illustrated in FIG. 4 and FIG. 5.

With reference now to FIGS. 6A-6C, a collection device 12 for use with an ANH blood collection system is provided. It is to be appreciated that the collection device 12 can be used in conjunction with the systems illustrated in FIGS. 4 and 5. The collection device 12, which is suitable for use with a standard donor or collection bag 18, includes a free-standing support 100 (also referred to as a frame or stand). The collection bag 18 can be secured to the support 100 such that the bag hangs without making contact with the ground or other support surface. In one embodiment, the support 100 includes a weighing device 110, such as spring scale. In this embodiment, the collection bag is hooked or otherwise secured to the spring scale such that the spring scale indicates the weight of the collection bag as blood is collected in the collection bag. This feature allows the user to monitor the volume of blood collected within the collection bag (based on the known density of whole blood and the amount of coagulant within the bag), thereby providing a relative accurate reading of the volume of whole blood and anticoagulant within the collection bag. In an alternative embodiment, the support 100 can include a "limiting" stand (e.g., an expanding stand such as an A-frame stand), that distends out a predetermined amount as to only allow a predetermined amount of fluid to be contained within the collection bag instead of using a scale. In one embodiment, the support 100 with scale 110 can include a stop, which prevents the bag from filling with fluid pass a certain predetermined volume.

Although, particular embodiments of the invention have been described in detail, it is understood that the invention is not limited correspondingly in scope, but includes all changes, modifications, and equivalents coming within the spirit and terms of the claims appended hereto. In addition, it is to be appreciated that features shown and described with respect to a given embodiment may also be used in conjunction with other embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An autologous normovolemic hemodilution (ANH) blood collection device of comprising:
   a canister having resilient, compressible sidewalls;
   a compression device operative to compress the canister, wherein the compression device includes a rotatable compression knob;
   wherein the resilient canister sidewalls are operative to return to an decompressed state following compression, thereby generating a negative pressure within the canister of sufficient magnitude to draw blood from a patient; and
   an agitator connected to a drive mechanism within the canister, wherein the drive mechanism includes a lower portion threadably engaging an upper portion, the upper portion being connected to the rotatable compression knob.

2. The device of claim 1, wherein the sidewalls include flexible outer wall members and an integral coil member.

3. The device of claim 1, wherein at least one of the internal portion of the sidewalls, the agitator and the drive mechanism are coated with an anticoagulant.

4. The device of claim 1, wherein the canister includes a blood reinfusion port and a blood input port.

5. A system for ANH blood collection comprising the device of claim 4, a blood collection line between a draw point on a patient and the blood input port on the device.

6. The system of claim 5, wherein the blood collection device is disposed at a vertical height that is at least as high as the vertical height of a draw point on the patient.

7. The system of claim 5, further comprising a pressure regulator disposed along the blood collection line in fluid communication with the patient and the blood collection device.

8. An autologous normovolemic hemodilution (ANH) blood collection device comprising:
   a canister having resilient, compressible sidewalls;
   a compression device operative to compress the canister;
   wherein the resilient canister sidewalls are operative to return to an decompressed state following compression, thereby generating a negative pressure within the canister of sufficient magnitude to draw blood from a patient; and
   an agitator connected to a drive mechanism within the canister, wherein the drive mechanism rotates as the canister returns to an uncompressed state, the rotation rotating the agitator within the canister.

* * * * *